US00PP29598P3

(12) United States Plant Patent
Smit

(10) Patent No.: US PP29,598 P3
(45) Date of Patent: Aug. 14, 2018

(54) ***PEPEROMIA* PLANT NAMED 'OBTIPAN'**

(50) Latin Name: *Peperomia obtusifolia*
Varietal Denomination: Obtipan

(71) Applicant: Obed Jacob Smit, Sappemeer (NL)

(72) Inventor: Obed Jacob Smit, Sappemeer (NL)

(73) Assignee: Eden Collection B.V., Sappemeer (NL)

( * ) Notice: Subject to any disclaimer, the term of this patent is extended or adjusted under 35 U.S.C. 154(b) by 0 days.

(21) Appl. No.: 15/330,478

(22) Filed: Sep. 26, 2016

(65) Prior Publication Data

US 2018/0092280 P1 Mar. 29, 2018

(51) Int. Cl.
*A01H 5/12* (2018.01)

(52) U.S. Cl.
USPC ..... Plt./373
CPC ..... *A01H 5/12* (2013.01)

(58) Field of Classification Search
USPC ..... Plt./373
See application file for complete search history.

(56) References Cited

PUBLICATIONS

PLUTO Plant Variety Database Aug. 30, 2017. p. 1.*
PLUTO Plant Variety Database Aug. 30, 2018. p. 1.*

* cited by examiner

*Primary Examiner* — Annette H Para

(57) ABSTRACT

A new cultivar of *Peperomia* plant named 'Obtipan' that is characterized by small rounded leaves that are green with brown margins.

1 Drawing Sheet

Botanical classification: *Peperomia obtusifolia.*
Variety denomination: 'Obtipan'.

BACKGROUND OF THE INVENTION

The present invention relates to a new and distinct cultivar of *Peperomia* plant botanically known as *Peperomia obtusifolia* and hereinafter referred to by the cultivar name 'Obtipan'.

'Obtipan' originated from the crossing of the female or seed parent, an unnamed *Peperomia obtusifolia* cultivar and the male or pollen parent, an unnamed *Peperomia obtusifolia* cultivar. The crossing was conducted in 2011 in Sappemeer, Netherlands. The resulting seeds were subsequently planted and grown. The cultivar 'Obtipan' was selected by the inventor in 2012 in a controlled environment as a single plant within the progeny of the stated cross in a cultivated area of Sappemeer, Netherlands.

Asexual reproduction of the new cultivar 'Obtipan' first occurred by tip cuttings from stems in 2012 in Sappemeer, Netherlands. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Peperomia* cultivar 'Obtipan'. These traits in combination distinguish 'Obtipan' as a new and distinct cultivar apart from other existing varieties of *Peperomia* known by the inventor.

1. *Peperomia* 'Obtipan' exhibits green leaves with brown margins.
2. *Peperomia* 'Obtipan' exhibits small rounded leaves.

The closest comparison cultivars are *Peperomia* 'Red Margin' (not patented) and *Peperomia* 'Variegata' (not patented). 'Obtipan' is distinguishable from 'Red Margin' by the following characteristics:

1. *Peperomia* 'Obtipan' exhibits green leaves with brown margins. In comparison, the leaves of 'Red Margin' are brown-green with brown-red margins.
2. *Peperomia* 'Obtipan' exhibits round shaped leaves. In comparison, the leaves of 'Red Margin' are more elongated in length.

'Obtipan' is distinguishable from 'Variegata' by the following characteristics:

1. *Peperomia* 'Obtipan' exhibits green leaves with brown margins. In comparison, the leaves of 'Variegata' are green with white margins.

'Obtipan' is distinguishable from the female parent plant, by the following characteristics:

1. *Peperomia* 'Obtipan' exhibits green leaves with brown margins. In comparison, the leaves of the female parent plant are green with no colored margins.

'Obtipan' is distinguishable from the male parent plant by the following characteristics:

1. *Peperomia* 'Obtipan' exhibits green leaves with brown margins. In comparison, the leaves of the male parent plant are green with no colored margins.
2. *Peperomia* 'Obtipan' exhibits small round shaped leaves. In comparison, the leaves of the male parent plant are larger and more elongated in length.
3. *Peperomia* 'Obtipan' exhibits leaf veins that are visible. In comparison, the leaf veins of the male parent plant are not visible.

BRIEF DESCRIPTION OF THE DRAWING

The accompanying photograph illustrates the distinguishing traits of *Peperomia* 'Obtipan'. The photograph shows an overall view of a 22 week old plant. The photograph was taken using conventional techniques and although colors may appear different from actual colors due to light reflectance, it is as accurate as possible by conventional photographic techniques.

BOTANICAL DESCRIPTION OF THE PLANT

The following is a detailed description of the new *Peperomia* cultivar named 'Obtipan'. Data was collected in Sappemeer, Netherlands from 22 week old plants grown in a glass greenhouse in 10.5 cm. diameter containers. The time of year was Winter and the temperature range was 18-25 degrees Centigrade during the day and 15-18 degrees Centigrade at night. The light level was natural light level. No photoperiodic treatments or growth retardants were used. Color determinations are in accordance with The Royal Horticultural Society Colour Chart 2015 edition, except where general color terms of ordinary dictionary significance are used. The growing requirements are similar to the species. 'Obtipan' has not been tested under all possible conditions and phenotypic differences may be observed with variations in environmental, climatic, and cultural conditions, however, without any variance in genotype.

Botanical classification: *Peperomia obtusifolia* 'Obtipan'.
Annual or perennial: Perennial.
Parentage: 'Obtipan' is a hybrid of the female parent, an unnamed *Peperomia obtusifolia* cultivar and the male parent an unnamed *Peperomia obtusifolia* cultivar.
Plant type: Potted plant.
Growth habit: Broad upright.
Plant shape: Flattened globe shaped.
Suitable container size: 7 cm. pots or larger.
Plant height: 14.4 cm.
Plant width: 21.5 cm.
Vigor: Low to moderate.
Low temperature tolerance: 10° Centigrade.
High temperature tolerance: 35° Centigrade.
Propagation: Stem tip cuttings.
Time to initiate roots (summer): 14 days at 18 to 20° C.
Time to initiate roots (winter): 21 days at 18 to 20° C.
Time to produce a rooted cutting: Cuttings are placed directly into growing pots.
Growth rate: Low to moderate.
Crop time: Approximately 4 to 5 months in Sappemeer, Netherlands.
Root system: Fine and fibrous.
Plant fragrance: None.
Stem:
- *Branching habit*.—Main and lateral branches.
- *Number of main branches per plant*.—Average 12.
- *Number of lateral branches per plant*.—Average 12.
- *Main branch dimensions*.—11.1 cm. in length and 0.6 cm. in diameter.
- *Internode length*.—1.0 cm.
- *Stem shape*.—Rounded.
- *Stem luster*.—Slightly glossy.
- *Stem pubescence*.—Absent.
- *Stem angle*.—Average 45 degrees.
- *Stem strength*.—Strong.
- *Stem color* (*young*).—200D, tinged 144B to 144C.
- *Stem color* (*mature*).—146B to 146C.
- *Internode color*.—146B to 146C, tinged 183C to 183D.

Foliage:
- *Leaf arrangement*.—Alternate.
- *Compound or single*.—Single.
- *Quantity of leaves per branch*.—Average 12.
- *Leaf shape*.—Orbicular to broad elliptic.
- *Leaf aspect*.—Slightly convex.
- *Leaf apex*.—Rounded.
- *Leaf base*.—Broad Attenuate.
- *Leaf dimensions*.—5.5 cm. in length and 5.1 cm. in width.
- *Texture*.—Smooth (both surfaces).
- *Leaf luster*.—Upper surface glossy, lower surface moderately glossy.
- *Pubescence*.—Absent.
- *Leaf margin*.—Entire.
- *Venation pattern*.—Pinnate, slightly furrowed.
- *Young leaf color* (*upper surface*).—Between NN137A and 141A.
- *Young leaf color* (*lower surface*).—Between 143C and 146B, margins 200D.
- *Mature leaf color* (*upper surface*).—Between NN137A and 139A.
- *Mature leaf color* (*lower surface*).—Between 143C and 146B, margins 200B to 200C.
- *Vein color* (*upper surface*).—144A.
- *Vein color* (*lower surface*).—143C.

Petiole:
- *Petiole dimensions*.—0.9 cm. in length and 0.35 cm. in diameter.
- *Petiole texture*.—Glabrous.
- *Petiole luster*.—Slightly glossy.
- *Petiole pubescence*.—Absent.
- *Petiole strength*.—Moderate.
- *Petiole color*.—177A to 177B.

Flower: 'Obtipan' has not produced flowers to date.
Fruit and seed: 'Obtipan' has not produced fruit or seed to date.
Disease and pest resistance: Disease and pest resistance has not been observed.

The invention claimed is:

1. A new and distinct variety of *Peperomia* plant named 'Obtipan' as described and illustrated.

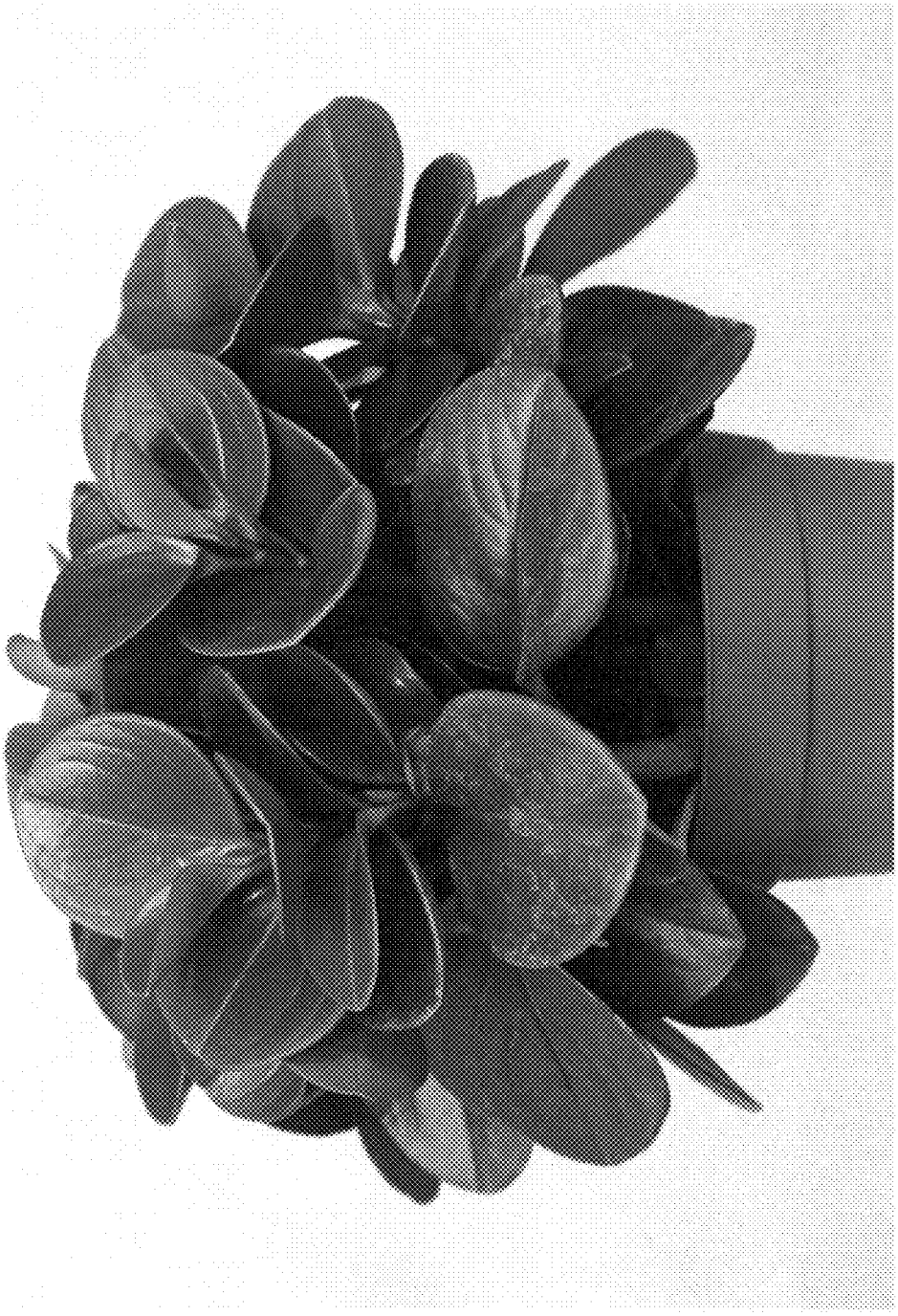

* * * * *